United States Patent [19]

Owyang

[11] Patent Number: 5,703,985
[45] Date of Patent: Dec. 30, 1997

[54] OPTICAL FIBER DEVICE AND METHOD FOR LASER SURGERY PROCEDURES

[75] Inventor: Zachary E. Owyang, Fremont, Calif.

[73] Assignee: Eclipse Surgical Technologies, Inc., Sunnyvale, Calif.

[21] Appl. No.: 638,677

[22] Filed: Apr. 29, 1996

[51] Int. Cl.⁶ .................. G02B 6/06; A61B 17/36
[52] U.S. Cl. .......... 385/117; 385/115; 385/116; 606/13; 606/14; 606/15; 606/16
[58] Field of Search ............... 385/115, 116, 385/117, 119, 43, 902; 606/13, 14, 15, 16, 7, 2; 607/17, 18

[56] References Cited

U.S. PATENT DOCUMENTS

| | | | |
|---|---|---|---|
| 3,556,085 | 1/1971 | Takahashi | 385/117 X |
| 4,641,912 | 2/1987 | Goldenberg | 385/117 X |
| 4,658,817 | 4/1987 | Hardy | 128/303.1 |
| 4,754,328 | 6/1988 | Barath et al. | 385/88 |
| 5,380,316 | 1/1995 | Aita et al. | 606/7 |
| 5,459,605 | 10/1995 | Kempf | 359/462 |
| 5,469,524 | 11/1995 | Esch et al. | 385/118 |
| 5,571,098 | 11/1996 | Domankevitz et al. | 606/15 |

*Primary Examiner*—Brian Healy
*Attorney, Agent, or Firm*—Owen, Wickersham & Erickson, P.C.

[57] ABSTRACT

A device for use in laser surgical procedures for moving axially an optical fiber bundle that is connected at its proximal end to a source of laser energy. The distal end of the fiber bundle has a generally tapered configuration so that it is capable of penetrating soft tissue of membrane such as the myocardium or epicardium of a human heart during the surgical procedure. Various combinations of bundled optical fiber elements are disclosed which provide different tapered distal end configurations used for various surgical procedures.

21 Claims, 4 Drawing Sheets

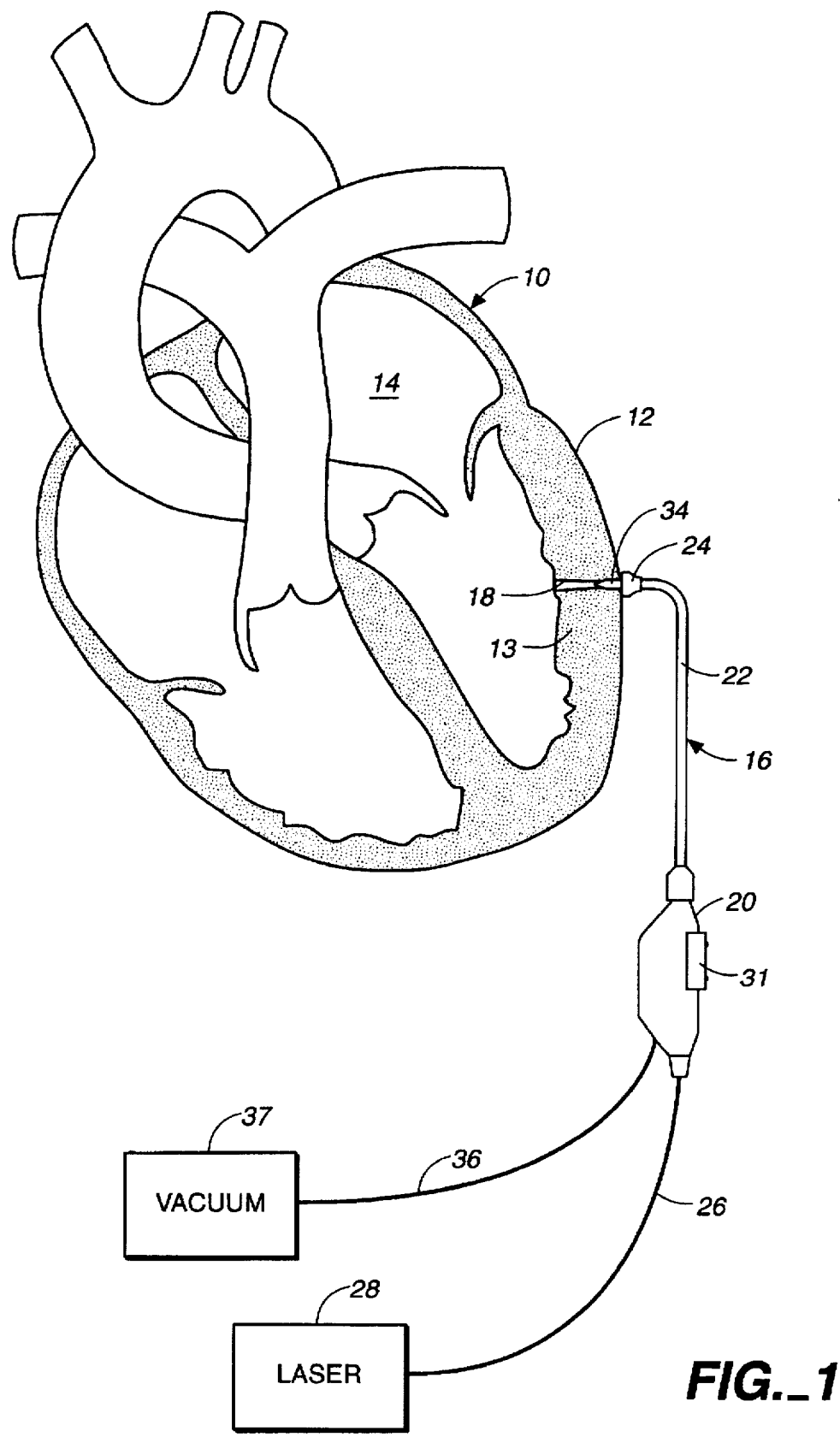
FIG._1

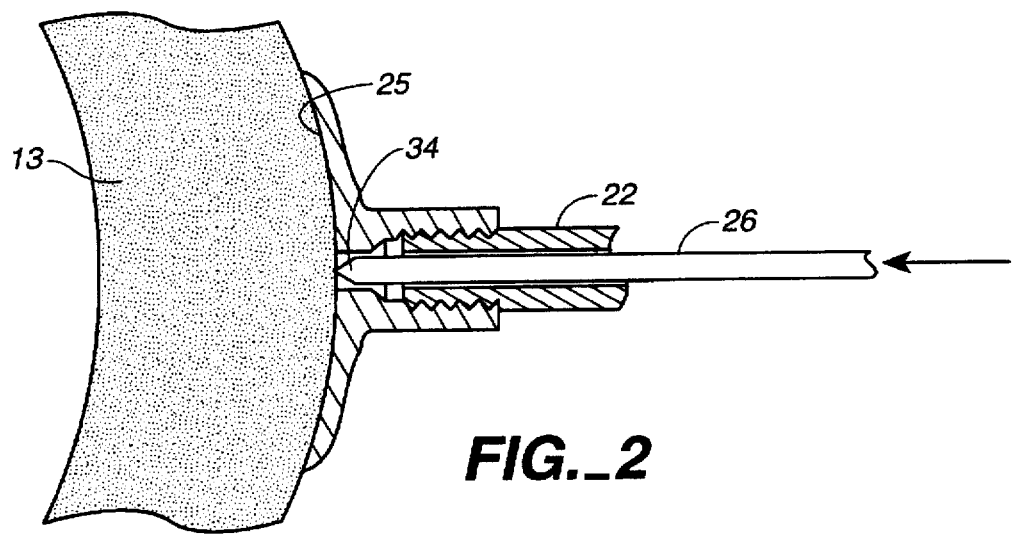
FIG._2
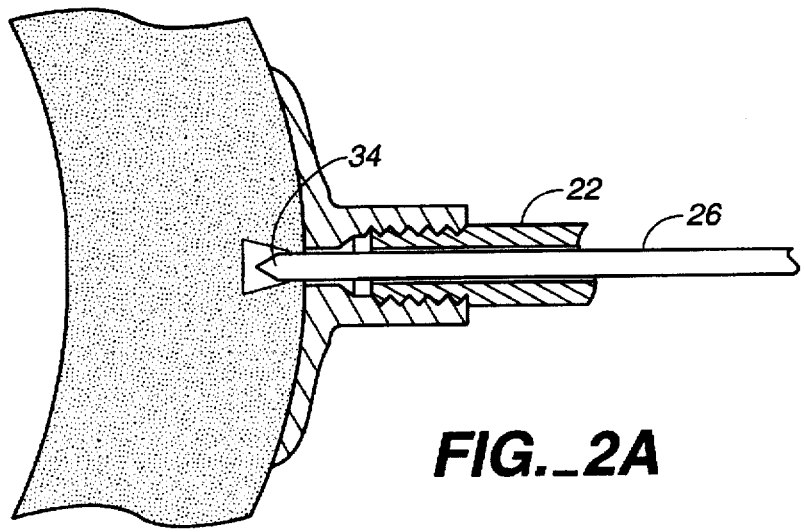
FIG._2A
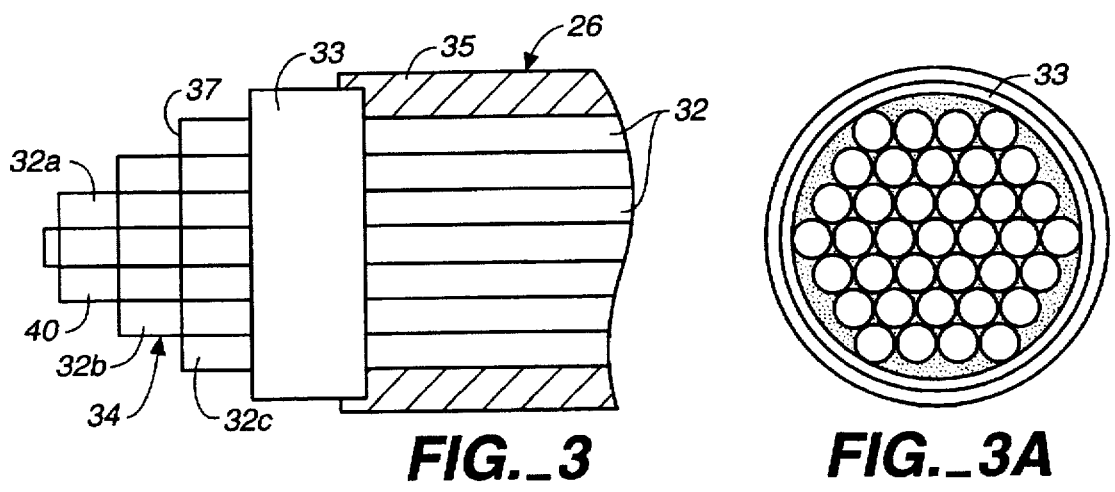
FIG._3  FIG._3A

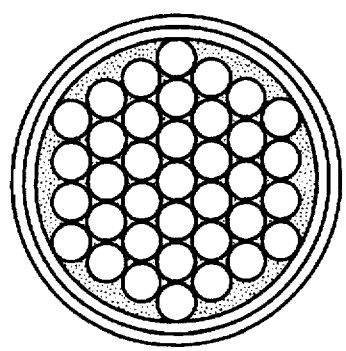
FIG._4A
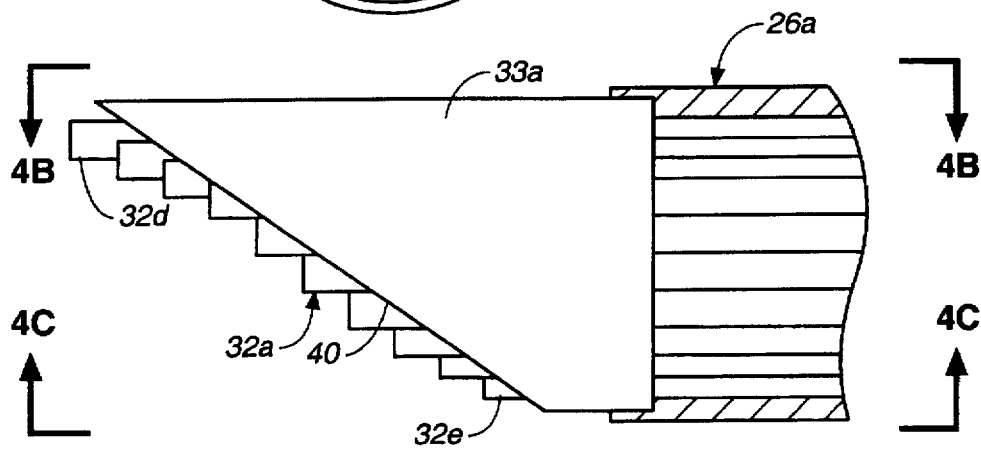
FIG._4
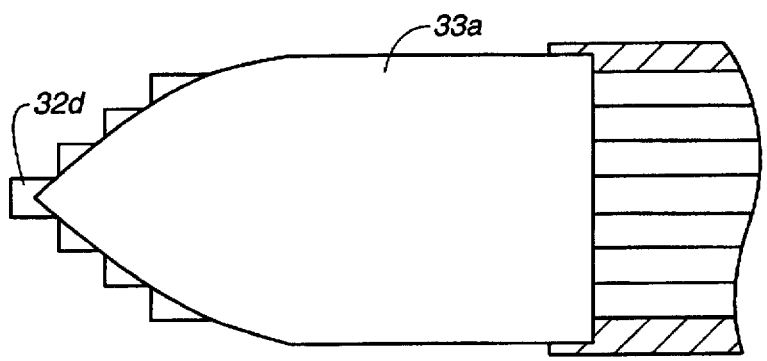
FIG._4B
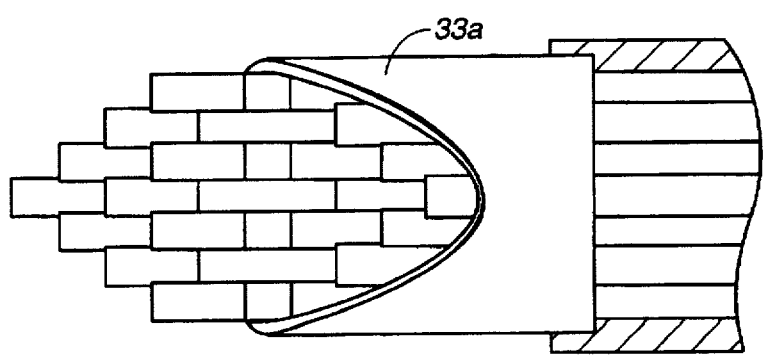
FIG._4C

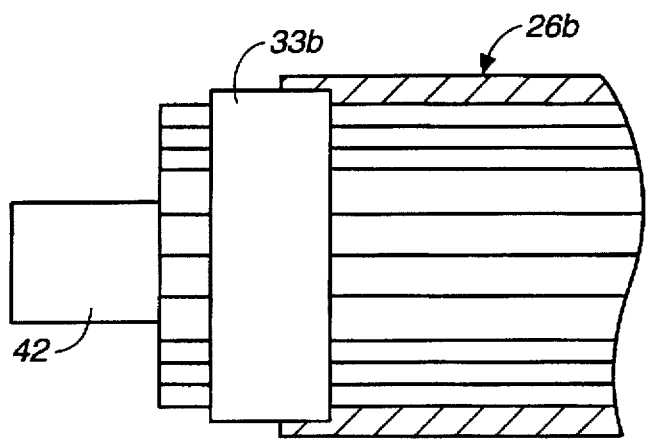 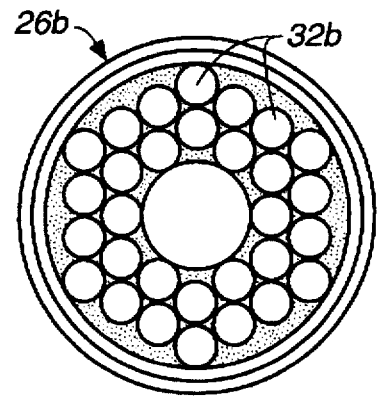
FIG._5  FIG._5A
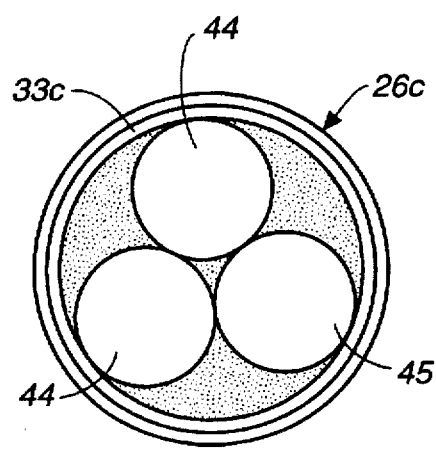
FIG._6A
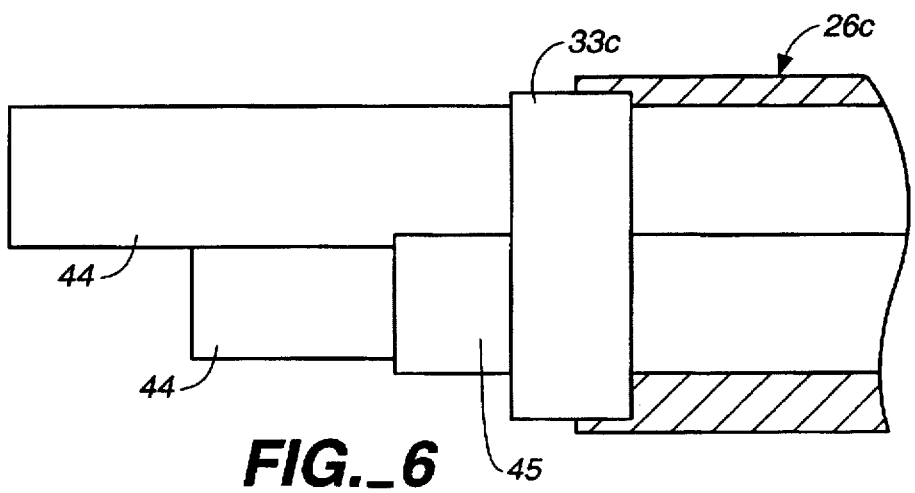
FIG._6

OPTICAL FIBER DEVICE AND METHOD FOR LASER SURGERY PROCEDURES

FIELD OF THE INVENTION

This invention relates to laser surgery and more particularly to optical fiber elements adaptable for penetrating tissue and thereafter transmitting and emitting laser energy from the distal tip of such elements. The invention also relates to a method for using optical fiber elements in a laser surgery procedure known as transmyocardial revascularization.

BACKGROUND OF THE INVENTION

Medical science has developed a wide variety of methods for counteracting the effects of cardiovascular disease including open heart and by-pass surgery. Non-surgical procedures such as percutaneous transliminal coronary angioplasty, laser angioplasty, and atherectomy have also been developed.

One alternative to the aforementioned procedures is known as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described in the above disclosure, a CO2 laser was used to produce channels in the ventricle from the epicardium through the myocardium. This procedure followed a surgical incision in the chest wall to expose the heart. Laser energy was transmitted from the laser directly to the epicardium by means Of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. A problem associated with the above procedure arose because laser perforation of the epicardium caused bleeding from the perforation outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al U.S. Pat. No. 5,380,316. Aita, commenting on the Hardy needle device, contended that mechanical piercing was undesirable because it entailed some degree of tearing of the pierced tissue, and that tearing often leads to fibrosis as the mechanical tear heals, a factor that severely diminishes the effectiveness of the TMR treatment. Aita, et al also contended that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini TMR procedure with respect to the aforementioned bleeding problem in the outer surface of the epicardium.

In a copending application Ser. No. 08/607,782, filed Feb. 27, 1996, bending, which is assigned to the assignee of the present application, an improved apparatus and method for TMR procedures is disclosed. In this application the epicardium membrane of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed, the opening that was made mechanically in the epicardium tends to close to prevent excessive bleeding from the channel formed in the myocardium.

Under certain operating conditions, the characteristics of the epicardium membrane may vary so the physician may elect to use an alternative piercing means for carrying out the aforesaid improved TMR procedure. In all cases, it is desirable that the physician be able to pierce the epicardium in the most efficient manner and thereby minimize the size of the opening necessary to accommodate the advancing fiber element. The present invention solves these problems.

It is therefore a general object of the present invention to provide an improved apparatus for performing laser myocardial revascularization that solves the problems of the aforementioned prior devices and procedures.

A further object of the present invention is to provide an optical fiber device for use in laser surgery procedures having a distal end that is configured to penetrate tissue with minimal axial force and also capable of emitting laser energy for ablating or stimulating tissue.

Another object of the invention is to provide an optical fiber device for laser surgery that has a tapered distal tip comprised of a plurality of bundled fiber members.

BRIEF SUMMARY OF THE INVENTION

In accordance with the principles of the present invention a fiberoptic laser catheter is provided which has a distal tip with a tapered configuration that enables it to penetrate tissue with only a small amount of axial force which the surgeon uses. For example, in a Transmyocardial Revascularization (TMR) procedure a plurality of channels are created in the myocardium tissue of a major heart chamber, e.g. the left ventricle. Each channel is formed by ablating myocardium tissue with laser energy from the distal end of a fiberoptic laser catheter. However, in order to minimize bleeding from outside the heart, it is preferable to first mechanically pierce the outer epicardium layer before laser energy is emitted as the catheter is moved forward.

In accordance with the present invention, the fiberoptic laser catheter is comprised of a plurality of single optical fibers that are arranged in parallel and bonded together in a bundle. At the distal end of the fiber bundle each optical fiber has a polished end face which is perpendicular to its longitudinal axis. Also, at the distal end certain individual fibers have different lengths so that the distal end of the bundle itself has a tapered configuration. The individual fibers are held firmly together by a bonding compound and are reinforced by a band of metal or plastic material that extends around the fiber bundle.

In use, the tapered distal end of the fiber bundle is sharp enough to penetrate tissue when moved forwardly with even a small axial force. For example, in a TMR procedure, the tapered end of a fiberoptic catheter according to the invention, can be used by the surgeon to pierce the epicardium membrane and move into the adjacent myocardium tissue before commencing to emit laser energy from the same tapered distal tip. As the fiberoptic catheter is moved forward, the emitted laser energy ablates the myocardium tissue to form a revascularization channel. When the catheter is withdrawn, the pierced hole in the epicardium which is much smaller than the ablated myocardium channel, tends to close to prevent any significant bleeding. The fiberoptic catheter with its tapered distal tip is also adaptable for use with other laser surgery procedures where initial piercing or penetration into tissue is required before laser energy is emitted from the distal tip.

Other objects, advantages and features of the invention will become apparent from the following detailed description of embodiments taken in conjunction with the accompanying drawing.

BRIEF DESCRIPTION OF THE DRAWING

FIG. 1 is a diagrammatic view showing a typical transmyocardial revascularization procedure on a heart utilizing principles of the present invention.

FIG. 2 is an enlarged view in section showing the distal end of a device for mechanically piercing the epicardium membrane of the heart with an optical fiber bundle according to the invention.

FIG. 2A is an enlarged view in section similar to FIG. 2 showing the optical fiber bundle after its tip has pierced the epicardium membrane.

FIG. 3 is a further enlarged view in elevation showing the tapered distal end of a fiberoptic bundle according to the invention.

FIG. 3A is an end view of the fiber optic bundle shown in FIG. 3.

FIG. 4 is an enlarged view in elevation showing an alternate form of a tapered distal end of a fiberoptic bundle.

FIG. 4A is an end view of the fiberoptic bundle of FIG. 4.

FIG. 4B is a tip view taken along line 4B—4B of the fiberoptic bundle of FIG. 4.

FIG. 4C is a bottom view of the fiberoptic bundle of FIG. 4.

FIG. 5 is a fragmentary view in elevation of another alternate form of a fiber optic bundle with a tapered distal end.

FIG. 5A is an end view of the fiberoptic bundle shown in FIG. 5.

FIG. 6 is a fragmentary elevation view of the distal end of another fiberoptic bundle embodying principles of the invention.

FIG. 6A is an end view of the fiber bundle shown in FIG. 6.

DETAILED DESCRIPTION OF EMBODIMENT

With reference to the drawing, FIG. 1 diagrammatically depicts a human heart 10 with the epicardium 12 of the left ventricle 14 exposed where a Transmyocardial Revascularization (TMR) procedure according to the invention is to be performed. Preliminary to the procedure the surgeon makes an incision in the patient's chest to expose the outer wall (epicardium) of the heart's left ventricle. In a human heart the wall of the left ventricle, is comprised of an outer layer or epicardium 12, the main muscle thickness, the myocardium 13, and the inner layer or endocardium. The epicardium is comprised of a smooth, moist serous membrane which is somewhat tougher than the other tissue layers of the heart muscle.

In carrying out the method of the present invention, the surgeon utilizes a hand-held device 16 which is manipulated and operated to form a series of revascularization channels 18 in the myocardium of the patient's heart at selected spaced apart locations.

In accordance with the principles of the invention, each of the channels 18 is formed by first piercing the epicardium membrane to form a relatively small opening using the tapered distal end 34 of an optical fiber bundle 26 that can be moved with axial force by means of a movable control member 31 on the device 16 operated by the surgeon. The fiber bundle is connected to a laser energy source 28 at its proximal end. Once through the epicardium opening, laser energy is emitted from the fiber bundle as it is moved forwardly to form the channel in the myocardium and completely through the endocardium. After the channel has been formed, the distal end of the fiber bundle is retracted to a position within an enlarged end member 24 of the device 16 which can then be moved to another location to repeat the procedure. When the distal end 34 of the fiber bundle is removed, the relatively small opening in the epicardium substantially closes due to the tissue resiliency, thereby minimizing any blood flow from the channel just formed.

As disclosed hereafter, the device may be connected by a flexible line 36 to a vacuum source 37 which helps to remove debris caused by laser action during a channel forming procedure and also to initiate blood flow into each channel as it is formed in order to maximize the revascularization process. It will be recognized by those skilled in the art that the device may be used with or without the vacuum source for providing suction.

As shown in FIG. 1, the device 16 comprises a housing 20 adapted to be hand held by the surgeon during an operative procedure, a neck member 22 attached to the housing and an enlarged interchangeable distal head member 24 having a central opening. An optical fiber bundle 26 whose proximal end is connected to the laser source 28 extends through the housing, through the neck member, and through the central opening in the distal end member 24. Within the housing 20 the fiber bundle 26 is connected to a movable shuttle (not shown) that extends outside the housing and is connected to a control member 31. Thus, movement of the control member 31 by the surgeon will move the distal end 34 of the fiber bundle beyond the distal head member 24 of the neck member. The vacuum line 36 extending from the vacuum source 37 such as a conventional hospital vacuum type canister device is connected to the housing 20. Within the housing the vacuum line communicates with an air passage around the fiber bundle that extends through the neck member 22 to the distal head member 24. Thus, when in use, a suction is provided at the distal head member 24 of the device 16 which performs two vital functions. First of all, as shown in FIG. 2, the suction force draws the epicardium tissue firmly against a contacting face 25 of the distal head member 24 so that a relatively small opening can be made in the epicardium muscle fibers by the distal end of the fiber bundle 26 to enable it to penetrate further and engage the myocardium before emitting laser energy. As the fiber bundle is advanced by the surgeon beyond the epicardium opening and into the myocardium 13, laser pulses are produced from its distal end 34 to form a channel 18 through the myocardium. As the fiber bundle continues to advance, the air suction provided helps to remove debris caused by the laser and also draws blood into the channel to assure that the revascularization process will commence properly. When the fiber bundle is retracted after forming a channel, the distal end member 24 is moved away and the opening in the epicardium closes naturally with a minimum of bleeding.

Any suitable means for advancing the fiber bundle with a controlled force sufficient to penetrate through the epicardium can be used. The device 16, as shown in FIG. 1, which is particularly adapted for this purpose is described in detail in the previously noted co-pending patent application. The disclosure of the aforesaid application is hereby incorporated by reference thereto.

The proximal end of the optical fiber bundle 26 is connected to the source or generator 28 of laser energy which is preferably a Holmium laser that operates at a wave length in the range of 1.8 to 2.2 microns and a pulse frequency in the range of 2–25 Hertz. This type of laser is preferable because it provides high absorption efficiency, hemostosis and a moderate absorption range in myocardium tissue, and is compatible with optical fiber delivery.

At the laser generator, laser energy is supplied to the optical fiber bundle 26 which, at its distal end, has a diameter of around 1 mm. In one typical form, shown in FIGS. 3 and 3A, the optical fiber bundle 26 is comprised of a plurality (e.g. 37) of individual glass fibers 32 each having a diameter of 100 microns. These glass fibers are held together by a suitable bonding material, such a 353 ND Epoxy, and near its distal tip, the bundle is preferably surrounded by an annular tantalum marker 33 which serves to retain the bundle in a closely packed geometric boundary. Surrounding the bundled fibers is a plastic protective sheath 35 having a wall thickness of approximately 0.004 inches. The sheath may be made of a metal material or plastic, such as polypropylene. The sheath further may be formed as a coil spring.

In accordance with the present invention, the tip of each optical fiber is polished to form an end face 37 that is perpendicular to its longitudinal axis so that a beam of laser energy is emitted axially from each fiber end face and the energy from adjacent fibers merge into a single beam. An important feature of the invention is that the tips of the optical fibers of the fiber bundle are spaced apart longitudinally so that the distal tip of the fiber bundle has a generally tapered configuration. This enables the fiber bundle to pierce the epicardium membrane to form an opening therein so that it can then be moved forward into the myocardium tissue before emitting laser energy to ablate tissue and form a channel 18.

In the embodiment of FIG. 3, a bundle 26 of optical fibers 32 has a tapered distal tip 34 that is formed by a cluster 40 of seven fibers 32(a) around the central axis of the bundle that are the longest of the bundle and extend a fixed predetermined distance, e.g. 0.025 mm beyond an adjacent intermediate ring of 12 fibers 32(b) which in turn extend the same distance, e.g. 0.025 mm beyond an outer ring of 18 fibers (32c). The aforesaid arrangement provides a distal end for a fiber bundle 26 which can emit a uniform beam of laser energy and yet has a structural configuration that will enable it to pierce and penetrate the epicardium membrane with a reasonable amount of axial force.

An alternate form of a tapered distal tip 34(a) according to the invention is illustrated in FIGS. 4–4C. Here, the fiber bundle 26(a) having a preselected number of optical fibers (e.g. 37), is held together by epoxy material and a metal or plastic material 33(a) which also serves as a marker. The individual fibers of the bundle vary in length along a plane 40 that intersects the axis of the bundle at an angle as shown in FIG. 4. Thus, the longest of the fibers 32(d) are at one side of the bundle and adjacent fibers are reduced progressively by a predetermined amount (e.g. 0.025 mm) toward the opposite side of the bundle where the shortest fiber 32(e) is shown. The resulting distal tip configuration of this arrangement is relatively sharp which readily enables it to penetrate the epicardium membrane with moderate axial force.

In the embodiment of FIGS. 5 and 5A, a single central fiber 42 having a diameter of 0.02 mm at the central axis of a bundle 26(b) is surrounded by a plurality (e.g. 30) of smaller fibers having a diameter of 0.01 mm. The central fiber 42 extends coaxially but approximately 0.032 mm longitudinally beyond the surrounding fibers 32(b). In this embodiment, the bundled fibers are again held together by an epoxy binder and a tantalum ring marker 33(b).

Another embodiment of a fiber bundle with a tapered tip configuration is shown in FIGS. 6 and 6A. Here, three relatively large fibers 44 and 45 having a diameter of 0.02–0.03 mm are held together in a bundle 26C by epoxy and a ring member 33(c). Beyond the ring member the tip ends of the three fibers extend for different lengths to provide a generally tapered distal tip configuration. Thus, the longest fiber extends 0.03–0.07 mm beyond an intermediate fiber which extends 0.03–0.07 mm beyond the shortest fiber 45.

It will be recognized by those skilled in the art that the number and diameters of fibers bundled in the various embodiments shown and described may vary. Accordingly, the angle formed at the tapered tip may vary and the distances between adjacent longer/shorter fibers also may vary. Additionally the use of potting materials around the bundled fibers also may affect the angle of taper.

In all of the aforesaid embodiments a bundle of optical fibers held tightly together are provided with a tapered distal tip configuration. When used with a suitable device such as the device 16, as shown, the tapered fiber bundle can first mechanically penetrate the epicardium membrane during a TMR procedure before emitting laser energy to form a revascularizing channel. Yet, when the fiber bundle is withdrawn the relatively small opening that it made in the epicardium will close naturally due to tissue resiliency and thus prevent excessive bleeding.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A device for use in laser surgical procedures comprising:

a plurality of optical fibers held together in parallel juxtaposition to form a flexible bundle having a proximal end adopted for connection with a source of laser energy; and a distal end wherein tips of said fibers are arranged at longitudinal distances apart so that said distal end of the bundle has a generally tapered configuration and is capable of penetrating soft tissue or membrane in order to emit laser energy within adjacent tissue.

2. The device as described in claim 1 for use in laser surgical procedures including potting means for bringing said fibers together to form a bundle and a band means around said bundle and spaced from said distal end.

3. The device as described in claim 1 for use in laser surgical procedures wherein said optical fibers all have tip faces which are perpendicular to the longitudinal axis of each fiber.

4. The device as described in claim 3 wherein said bundle is comprised of concentric multiple optical fibers including a central fiber means having tip face spaced farthest from said band means, an outer ring having tip faces spaced nearest to said band means, and an intermediate ring having tip faces spaced in between said tip faces of said central fiber means and said outer ring.

5. The surgical device of claim 4 wherein said central fiber means is comprised of a single central fiber surrounded by six fibers of the same diameter, said fibers having a diameter of around 0.01 mm.

6. The surgical device of claim 4 wherein said central optical fiber means comprises one fiber element having a diameter of between 0.01–0.02 mm.

7. The surgical device of claims 5 and 6 wherein said outer ring has a total of 18 fibers and said intermediate ring has a total of 12 fibers, all of said fibers having a diameter of around 1 mm.

8. The surgical device of claim 7 wherein said band is generally tubular and is made of tantalum.

9. The surgical device of claim 4 where the end faces of said intermediate ring are spaced about 0.02 to 0.03 mm from said end faces of said central fiber means and said outer ring of fiber members.

10. The surgical device of claim 3 wherein a fiber on one side of said fiber bundle is the longest fiber and a fiber on the opposite side is the shortest fiber of the bundle and the intermediate fibers between said longest and shortest fibers have end faces that terminate generally along a plane that cuts diagonally at a preselected angle across said bundle and across the end faces of said longest and shortest fibers, thereby providing said distal end of said fiber bundle with a generally tapered configuration.

11. The surgical device of claim 10 wherein said preselected angle is around 60° relative to the longitudinal axis of said fiber bundle.

12. The surgical device of claim 10 wherein the end faces of adjacent fibers along said plane are spaced apart by 0.02 to 0.03 mm.

13. The surgical device of claim 10 wherein said band means has a triangular shape with a pointed portion that extends over all of the outer fiber members.

14. The surgical device of claim 10 wherein said fiber bundle is comprised of three optical fibers each having a diameter of around 0.02–0.03 mm.

15. The surgical device of claim 14 wherein the end faces of said fiber members are spaced apart a distance of 0.03–0.04 mm.

16. A method for revascularizing a desired portion of a patient's heart, comprising the steps of:

providing a flexible laser catheter comprised of a plurality of optical fiber members having longitudinally spaced apart tips to provide said catheter with a generally tapered distal end;

placing said distal end of the catheter against the epicardium of the patient's heart and moving it forward to form an opening through the epicardium and into the myocardium;

moving said distal end of said catheter inwardly from said opening and emitting laser energy from said distal end to ablate myocardium tissue and form a funnel-shaped channel extending through the myocardium and the endocardium of the heart;

retracting said catheter through the myocardium channel; and removing said tapered distal end of the catheter from the epicardium to close said opening therein to prevent excessive bleeding therefrom.

17. The method as described in claim 16 where said laser energy emitted from said distal end is a pulsed holmium laser operating a wave length of 1.8 to 2.2 microns and a pulse rate in the range of 2–25 pps.

18. The method as described in claim 16 wherein said catheter comprises:

a plurality of optical fibers held together in parallel juxtaposition to form a flexible bundle having a distal end, band means around said bundle and spaced from said distal end, and a proximal end adapted for connection with a source of laser energy; and a distal end wherein tips of said fibers are arranged at distances apart so that said distal end has a generally tapered configuration and is capable of penetrating soft tissue or membrane in order to emit laser energy within adjacent tissue.

19. The method as described in claim 18 wherein said bundle is comprised of concentric multiple optical fibers including a central fiber means having its tip faces spaced farthest from said band means, an outer ring having tip faces spaced nearest to said band means, and an intermediate ring having tip faces spaced in between said tip faces of said central fiber means and said outer ring.

20. The method as described in claim 18 wherein a fiber on one side of said fiber bundle is the longest fiber and a fiber on the opposite side is the shortest fiber of the bundle and the intermediate fibers between said longest and shortest fibers have end faces that terminate generally along a plane that cuts diagonally at a preselected angle across said bundle and across the end faces of said longest and shortest fibers, thereby providing said distal end of said fiber bundle with a generally tapered configuration.

21. The method as described in claim 18 wherein said fiber bundle is comprised of three optical fibers each having a diameter of around 0.02–0.03 mm.

* * * * *